United States Patent
Bastiani et al.

(10) Patent No.: US 9,919,985 B2
(45) Date of Patent: Mar. 20, 2018

(54) ADDITIVES FOR MAXIMIZING LIGHT OLEFINS IN FLUID CATALYTIC CRACKING AND PROCESS UNITS

(76) Inventors: Raquel Bastiani, Rio de Janeiro (BR); Lam Yiu Lau, Rio de Janeiro (BR); Andrea de Rezende Pinho, Rio de Janeiro (BR); Rosana Wasserman, Rio de Janeiro (BR); Ivanilda Barboza do Espirito Santo, Rio de Janeiro (BR)

(*) Notice: Subject to any disclaimer, the term of this patent is extended or adjusted under 35 U.S.C. 154(b) by 560 days.

(21) Appl. No.: 14/382,477

(22) PCT Filed: Mar. 2, 2012

(86) PCT No.: PCT/BR2012/000055
§ 371 (c)(1),
(2), (4) Date: Sep. 2, 2014

(87) PCT Pub. No.: WO2013/126974
PCT Pub. Date: Sep. 6, 2013

(65) Prior Publication Data
US 2015/0094511 A1    Apr. 2, 2015

(51) Int. Cl.
| | |
|---|---|
| *C07C 4/06* | (2006.01) |
| *C10G 11/05* | (2006.01) |
| *C10G 11/18* | (2006.01) |
| *B01J 29/80* | (2006.01) |
| *B01J 29/40* | (2006.01) |
| *B01J 29/65* | (2006.01) |
| *B01J 29/18* | (2006.01) |

(52) U.S. Cl.
CPC ............. *C07C 4/06* (2013.01); *B01J 29/80* (2013.01); *C10G 11/05* (2013.01); *C10G 11/18* (2013.01); *B01J 29/18* (2013.01); *B01J 29/40* (2013.01); *B01J 29/65* (2013.01); *C07C 2529/85* (2013.01); *C10G 2400/20* (2013.01)

(58) Field of Classification Search
CPC .......................................................... C07C 4/06
USPC ................... 585/648, 649, 650, 651, 653
See application file for complete search history.

(56) References Cited

U.S. PATENT DOCUMENTS

| | | |
|---|---|---|
| 4,976,847 A | 12/1990 | Maxwell et al. |
| 6,867,341 B1 | 3/2005 | Abrevaya et al. |
| 2009/0107885 A1 | 4/2009 | Bastiani et al. |
| 2010/0076096 A1* | 3/2010 | Calis ............... C10G 11/18 518/702 |
| 2010/0105974 A1 | 4/2010 | Towler et al. |

FOREIGN PATENT DOCUMENTS

| | | |
|---|---|---|
| BR | PI 8904248 A | 4/1990 |
| BR | PI 0704422-4 A2 | 6/2009 |
| WO | 2006/098712 A1 | 9/2006 |

OTHER PUBLICATIONS

International Search Report of PCT/BR2012/000055 dated May 15, 2012.
Written Opinion of the International Searching Authority of PCT/BR2012/000055 dated May 15, 2012.

* cited by examiner

*Primary Examiner* — Thuan D Dang
(74) *Attorney, Agent, or Firm* — Sughrue Mion, PLLC

(57) ABSTRACT

Additives for mixing into the base catalyst inventory of the fluid catalytic cracking (FCC) process units, so as to achieve a high selectivity of light olefins (ethylene and propylene), are described. Such additives comprise an FER zeolite and an MFI zeolite, the MFI zeolite preferably being zeolite ZSM-5. The mixture of the additive in a concentration greater than 2% w/w relative to the base catalyst of an FCC unit allows greater selectivity for light olefins, propylene and ethylene, while maintaining catalytic activity.

6 Claims, No Drawings

ADDITIVES FOR MAXIMIZING LIGHT OLEFINS IN FLUID CATALYTIC CRACKING AND PROCESS UNITS

CROSS REFERENCE TO RELATED APPLICATIONS

This is a National Stage of International Application No. PCT/BR2012/000055 filed Mar. 2, 2012, the contents of which are incorporated herein by reference in their entirety.

FIELD OF THE INVENTION

This invention pertains to the field of additives for use in hydrocarbon fluid catalytic cracking (FCC) processes, more specifically additives containing a mixture of ferrierite and MFI zeolites for use in FCC units, operating under highly severe conditions, for increasing yields of light olefins, particularly ethylene and propylene.

BACKGROUND OF THE INVENTION

The fluid catalytic cracking (FCC) process is responsible for a third of the propylene produced in the world today. The advent of petrochemical FCC processes contributed to significantly increasing the production of both propylene and ethylene. Such processes classically use Y and MFI zeolite-based catalysts, varying the concentration of these according to the load and the characteristics of the process used.

The FCC processes currently used that focus on the production of light olefins exhibit a production limit of about 20% w/w of ethylene and 24% w/w of propylene, and also produce a significant amount of aromatics (about 18% w/w). Thus, a new catalyst system aimed at greater production of light olefins, while simultaneously minimizing the formation of aromatic compounds, is highly desirable.

More recently, there have been publications proposing the use of FER-based additives to increase the production of light olefins (ethylene and propylene) in FCC units. For example, U.S. Pat. No. 6,867,341 discloses a process for fluid catalytic cracking of a naphtha feedstock operating at temperatures from 650° C. to 670° C. The process uses a high Si/Al ratio zeolite FER-based additive. Examples in the mentioned document demonstrate that FER zeolite possesses high selectivity to ethylene and propylene in comparison with the other zeolites examined, such as beta, omega, mordenite, EU-1, SUZ-4, ZSM-22 and ZSM-23.

Along the same lines, we have document WO 2006/098712, which discloses a naphtha fluid catalytic cracking process operating at temperatures from 600° C. to 675° C., using pure FER as an additive. The use of FER as an additive promotes high selectivity to ethylene and propylene with low formation of aromatics. That document compared the use of FER as an additive in FCC processes with the use of other zeolites as additives, including beta, omega, mordenite, EU-1, ZSM-22, ZSM-23, SUZ-4 and MFI zeolites.

Although the FER zeolite exhibits high selectivity to ethylene and propylene with reduced production of aromatics, it exhibits lower catalytic activity than do the zeolites usually employed for maximizing light olefins, such as MFI-type zeolites, due to the fact that its pore openings consist of rings of eight and ten members, which is significantly less when compared to those of the MFI zeolites.

U.S. Document 2010/0105974 discloses a fluid catalytic cracking process of a naphtha feedstock operating at reaction temperatures above 650° C. The document discloses the use of a mixture of catalysts as an additive to the base catalyst in an FCC process. This mixture comprises a first catalyst based on a zeolite with small pores having a pore opening of 3 to 5 Å, which can be Rho, chabazite, ZK-5, ITQ-3, ZK-4, erionite, ferrierite, chinoptilolite, ZSM-22 and mixtures thereof, and a second catalyst based on an intermediate pore zeolite with a pore opening of 5 to 5.5 Å, this zeolite being MFI-type and designated by the authors as nano-silicalite. The zeolite should have a silica-alumina ratio greater than 200.

The use of a catalyst system using the mixture of FER zeolites and nano-silicalite as an additive, however, does not produce a higher yield of light olefins when compared with the use of pure nano-silicalite. Accordingly, the document discloses the use of the mixture for the sole purpose of changing the ethylene/propylene ratio, thus maximizing the production of ethylene, to the detriment of propylene production.

Therefore, the technique still requires additives for use in FCC processes that maximize production of light olefins, particularly ethylene and propylene, and that exhibit high activity, as described in detail below.

SUMMARY OF THE INVENTION

The present invention provides additives for use in fluid catalytic cracking (FCC) processes operating in highly severe conditions, to produce high selectivity with light olefins, particularly ethylene and propylene.

Such additives comprise the mixture of ferrierite (FER) and MFI zeolites at an FER/MFI mass ratio of at least 0.5:1, and exhibit high activity, without loss of selectivity in relation to the propylene, when compared with conventional additives, such as the additives comprising only MFI-type zeolites (ZSM-5).

DETAILED DESCRIPTION OF THE INVENTION

Broadly speaking, the invention concerns additives applicable to maximizing light olefins in fluid catalytic cracking (FCC) process units.

Such additives are comprised of a mixture of FER zeolite and MFI zeolites and, where FER/MFI mass ratio is at least 0.5:1, where the additives are added to the base catalyst inventory of an FCC process, so that the final concentration of the additive in relation to the base catalyst inventory is greater than 2% w/w.

In the present invention a final concentration of MFI zeolite is used, which can be selected from a ZSM-5 or ZSM-11 zeolite, greater than 1% w/w relative to the base catalyst inventory of an FCC unit.

In the mixture of MFI zeolites and FER zeolites, there is a synergistic effect between them, as the FER zeolite reduces the contribution of the hydrogen transfer reactions promoted by MFI zeolites that are responsible for the generation of propane, thus improving the selectivity with respect to light olefins, particularly the selectivity with ethylene and propylene, as is apparent from the results obtained in Example 3 described below.

Another aspect of the invention is an FCC process on hydrocarbon feedstock for maximizing light olefins, particularly the ethylene and propylene, where the yield of light olefins is controlled by the effect of mixing an additive into the base catalyst inventory of the process.

The feedstocks of hydrocarbon streams can be selected from among typical feedstocks for FCC processes, such as a naphtha, kerosene, diesel or gas oil stream, as well as any other effluent from petroleum distillation or refining units, such as delayed coking units, hydrocracking units, and hydrotreating units.

Recycles of C4 and C5 streams of refining units, such as fluid catalytic cracking units, delayed coking units, hydrocracking units and hydrotreating units, can also be used as feedstock.

Hydrocarbon feedstocks of the LPG, naphtha, kerosene, diesel or gas oil type, preferably feedstocks exhibiting initial boiling points above −11° C., are preferred for the process. For an FCC process unit, the cracking conditions include catalyst/oil ratio between 10 and 50 and temperatures between 550° C. and 750° C.

Also in relation to the FCC process, the base catalyst to be used may be a Y zeolite-based catalyst, such as a porous matrix containing alumina, silica-alumina, clay or the like.

Thus, an additive of the present invention can be mixed into the catalyst inventory of an FCC process, for the purpose of maximizing the yield of light olefins. This mixture must maintain a final additive concentration above 2% w/w in relation to the base catalyst inventory of the unit, without significantly altering the activity of the base FCC catalyst.

EXAMPLES

Examples of the invention described below are purely illustrative and are intended to demonstrate that the intrinsic capability of the additive containing both zeolites, FER and MFI, to achieve the above-mentioned performance, is superior to conventional additives containing only MFI zeolites, without limiting the range of MFI and FER contents to be applied, as well as the way in which these zeolites are incorporated, as separate particles or in combination.

In all the following examples, zeolites in proton form are mixed with the base catalyst (E-Cat) and tested in a catalytic cracking unit with a fixed bed type reactor. The adopted reaction temperature is 600° C. and a typical Brazilian gas oil is used as feedstock. The catalyst mass and the feedstock mass are fixed at 9 g and 1.8 g, respectively, consequently maintaining the catalyst/oil ratio at 5. Primarily, the effect of these zeolites on the yield of light olefins in the petrochemical interest (ethylene and propylene) is evaluated. All the catalysts are evaluated twice.

The catalytic test begins with the injection of feedstock into the preheated bed at the desired temperature. The products are collected in an ampoule immersed in a bath at −10° C. At the end of the feedstock injection, a continuous flow of nitrogen is maintained in order to remove any product contained in the catalyst bed. After completion of this rectification of the bed, the liquid is collected from the ampoule and weighed. The liquid product is then analyzed by gas chromatography by means of the Simulated Distillation or SD (ASTM D 2877) method.

The SD enables the identification of the following products: naphtha (<216.4° C.); light cycle oil [LCO] (216.4° C.<LCO<344° C.); and the residue (>344° C.). The gaseous product formed is determined by the volume of it formed and by quantifying the gas by a gas chromatography. The coked catalyst is removed from the reactor at the end of the catalytic test. The coke formed on the catalyst is then quantified in a LECO CS-244 carbon analyzer. The coke is burned in this unit until it is completely converted to CO2, which is then analyzed by means of an infrared analyzer.

Table 1 below shows a summary of the operating conditions used in the catalytic test.

TABLE 1

| | |
|---|---|
| CTO | 5 |
| Injection rate | 0.02 g/s |
| Catalyst mass | 9 g |
| Injection time | 90 s |
| Injected feedstock mass | 1.8 g |
| Reaction temperature | 600° C. |
| Catalyst stripping time | 360 s |
| Liquid stripping time | 630 s |
| $N_2$ flow on the feedstock line (descending)* | 20 sccm |
| $N_2$ flow in the injection (descending)** | 20 sccm*** |
| Auxiliary $N_2$ flow in the injection (descending) | 60 sccm*** |

*$N_2$ injection together with the feedstock.
**Injection of auxiliary $N_2$, so as not to coke the feedstock injector.
***sccm - standard cubic centimeters per minute The base catalyst (E-cat) used in the catalytic tests is a typical commercial equilibrium catalyst of an FCC unit, the properties of which are shown in Table 2.

Table 2 also contains the description of the chemical and textural properties of the MFI and FER zeolites used in the catalytic tests presented.

The feedstock used was a gas oil, the properties of which are shown in Table 3.

TABLE 2

| Catalyst/zeolites | E-cat (base) | MFI | FER |
|---|---|---|---|
| BET area (m²/g) | 148 | 375 | 330 |
| Micropore volume | 0.0457 | 0.128 | 0.135 |
| Chemical analysis | | | |
| $Al_2O_3$ (% w/w) | 47.9 | 4.4 | 7.9 |
| $SiO_2$ (% w/w) | 47.6 | 95.1 | 91.5 |
| $RE_2O_3$ (% w/w) | 2.82 | 0.0 | 0.0 |
| $Na_2O$ (% w/w) | 0.26 | 0.02 | 0.0 |
| $P_2O_5$ (ppm) | 6116 | 0.0 | 0.0 |
| Ni (ppm) | 1013 | 0.0 | 0.0 |
| V (ppm) | 1391 | 0.0 | 0.0 |
| SAR * (mol/mol) | — | 25.0 | 21.7 |
| Activity for the n-hexane cracking ** (min. n-hexane mol/g) | — | 959 | 447 |

* SAR = silica/alumina ratio
** Reaction conditions: quartz fixed bed microreactor; temperature of 500° C.; atmospheric pressure; 0.02 g catalyst mass; n-hexane/nitrogen ratio of 0.16; and flow of 30 ml/min.

TABLE 3

| | |
|---|---|
| Density at 20/4° C. | 0.8406 |
| ° API | 36.1 |
| Sulfur (ASTM D-5354) (ppm) | 508 |
| Distillation (ASTM D-2887) | |
| IBP (° C.) | 97.0 |
| T50% (° C.) | 275 |
| FBP (° C.) | 449.5 |
| Liquid chromatography | |
| Saturates | 65.5 |
| Olefins | 2.0 |
| Monoaromatics | 26.7 |
| Diaromatics | 3.9 |
| Polyaromatics | 1.9 |
| Total aromatics | 32.5 |
| NMR hydrogen | 13.27 |
| RMN of the C-13 | |
| Unsaturated carbon | 15.5 |
| Saturated carbon | 84.5 |
| Alkyl aromatic carbon | 4.9 |

TABLE 3-continued

| | |
|---|---|
| Aromatic carbon | 7.6 |
| Aromaticity factor | 0.155 |

Example 1

Example 1 illustrates the production of light olefins of petrochemical interest (ethylene plus propylene), the yield of which attains its limit (20.3% w/w) with the sole use of 1% w/w pure MFI for the E-cat. For contents above 1% MFI in the mixture a significant reduction is noted in the production of light olefins, accompanied by a significant increase in the propane yield.

Table 4 below presents the results of catalytic tests using an MFI-type zeolite as an additive to the base catalyst (E-cat) of an FCC unit.

TABLE 4

| CATALYST | E-cat | 0.5% MFI | 1% MFI | 2% MFI | 4% MFI | 8% MFI |
|---|---|---|---|---|---|---|
| Conversion (% w/w) | 87.4 | 87.6 | 86.9 | 89.5 | 88.9 | 88.0 |
| Ethylene (% w/w) | 2.7 | 5.8 | 7.0 | 8.4 | 9.3 | 8.3 |
| Propylene (% w/w) | 8.8 | 13.4 | 13.2 | 11.1 | 10.8 | 8.1 |
| Ethylene + propylene (% w/w) | 11.5 | 19.2 | 20.3 | 19.5 | 20.1 | 16.4 |
| Butenes (% w/w) | 5.8 | 6.3 | 5.9 | 4.8 | 4.2 | 2.7 |
| Propane (% w/w) | 3.9 | 5.7 | 6.4 | 10.2 | 11.4 | 14.6 |
| Paraffin/olefin ratio | 1.1 | 0.8 | 0.9 | 1.2 | 1.2 | 1.6 |
| Fuel gas (% w/w) | 8.5 | 11.3 | 12.5 | 16.0 | 17.3 | 19.3 |
| LPG (% w/w) | 28.7 | 36.1 | 36.4 | 37.5 | 36.0 | 31.8 |
| Gasoline (% w/w) | 44.8 | 34.4 | 32.4 | 28.8 | 29.6 | 31.4 |
| LCO (% w/w) | 10.3 | 9.6 | 9.9 | 8.7 | 8.7 | 9.5 |
| Bottom Matter (% w/w) | 2.2 | 2.7 | 3.2 | 1.8 | 2.3 | 2.5 |
| Coke (% w/w) | 5.4 | 5.8 | 5.6 | 7.2 | 6.0 | 5.5 |

Example 2

Example 2 illustrates the sole use of FER in an admixture with E-cat, which cannot attain the same level of light olefin yield obtained with an additive consisting of an MFI zeolite alone (shown in Example 1). However, the use of the FER allows a reduction in hydrogen transfer reactions with a reduced paraffin/olefin ratio. Furthermore, the addition of any FER concentration to the E-cat does not increase the production of propane, as observed for the MFI zeolite (shown in Example 1).

Table 5 below shows the results of catalytic tests using FER zeolite alone as an additive to a (E-Cat) base catalyst of an FCC unit.

TABLE 5

| CATALYST | E-cat | 2% FER | 4% FER | 6% FER | 8% FER |
|---|---|---|---|---|---|
| Conversion (% w/w) | 87.4 | 86.8 | 86.9 | 87.4 | 87.7 |
| Ethylene (% w/w) | 2.7 | 3.9 | 5.2 | 5.7 | 6.1 |
| Propylene (% w/w) | 8.8 | 10.2 | 12.3 | 12.1 | 12.2 |
| Ethylene + propylene (% w/w) | 11.5 | 14.1 | 17.5 | 17.8 | 18.3 |
| Butenes (% w/w) | 5.8 | 5.7 | 6.1 | 5.4 | 5.2 |
| Propane (% w/w) | 3.9 | 4.2 | 4.3 | 4.2 | 4.2 |
| Paraffin/olefin ratio | 1.1 | 1.0 | 0.8 | 0.8 | 0.8 |
| Fuel gas (% w/w) | 8.5 | 9.7 | 11.3 | 11.4 | 11.9 |
| LPG (% w/w) | 28.7 | 29.6 | 32.3 | 30.9 | 30.4 |
| Gasoline (% w/w) | 44.8 | 41.3 | 38.9 | 38.9 | 39.4 |
| LCO (% w/w) | 10.3 | 10.6 | 10.2 | 10.5 | 10.1 |
| Bottom matter (% w/w) | 2.2 | 2.5 | 2.9 | 2.1 | 2.2 |
| Coke (% w/w) | 5.4 | 6.3 | 4.5 | 6.1 | 5.9 |

Example 3

Example 3 illustrates the use of a mixture of MFI and FER zeolites as an additive to the E-cat, making it possible to exceed the production limit of light olefins previously achieved through the use of pure MFI and FER zeolites. Thus, the use of the MFI and FER mixture as an additive in the catalytic cracking process enabled light olefins to be obtained with conversions between 21.4% w/w and 22.2% w/w, while the use of pure MFI zeolite attained 20.3% w/w (shown in Example 1) and pure FER, 18.2% w/w (shown in Example 2).

All the aforementioned examples describe catalytic tests performed in the same conditions.

The mixture of FER and MFI zeolites used the same zeolites previously evaluated in their pure form. Thus, it is possible to demonstrate that there is a synergistic effect on the production of light olefins when using the FER and MFI mixture as an additive to an FCC base catalyst. When added to the catalytic system, both zeolites contribute to the production of light olefins; however, the presence of FER zeolite reduces the production of paraffins, primarily propane, thus avoiding the consumption of propylene due to hydrogen transfer, and thereby improving the performance of the ZSM-5/FER mixture relative to the use of pure MFI.

Table 6 below presents the results of the catalytic tests using additives, including MFI and FER zeolites, mixed into the (E-cat) base catalyst of an FCC unit.

TABLE 6

| CATALYST | E-cat | 1% MFI + 1% FER | 1% MFI + 2% FER | 2% MFI + 2% FER |
|---|---|---|---|---|
| Conversion (% w/w) | 87.4 | 88.7 | 88.2 | 89.2 |
| Ethylene (% w/w) | 2.7 | 9.1 | 8.2 | 8.1 |
| Propylene (% w/w) | 8.8 | 13.1 | 13.3 | 13.5 |
| Ethylene + propylene (% w/w) | 11.5 | 22.2 | 21.4 | 21.6 |
| Butenes (% w/w) | 5.8 | 5.5 | 5.9 | 6.0 |
| Propane (% w/w) | 3.9 | 8.0 | 7.3 | 7.3 |
| Paraffin/olefin ratio | 1.1 | 0.9 | 0.9 | 0.9 |
| Fuel gas (% w/w) | 8.5 | 16.3 | 14.6 | 14.1 |
| LPG (% w/w) | 28.7 | 38.0 | 37.2 | 37.8 |
| Gasoline (% w/w) | 44.8 | 28.8 | 30.1 | 31.2 |
| LCO (% w/w) | 10.3 | 8.8 | 9.1 | 8.5 |
| Bottom matter (% w/w) | 2.2 | 2.5 | 2.7 | 2.3 |
| Coke (% w/w) | 5.4 | 5.7 | 6.4 | 6.1 |

The invention claimed is:
1. An FCC process for maximizing light olefins, comprising:
   mixing an additive for maximizing light olefins into a base catalyst inventory to form a mixed catalyst; and feeding a hydrocarbon feedstock to a reactor containing the mixed catalyst and catalytically cracking the hydrocarbon feedstock, wherein the additive comprises an MFI and FER zeolite mixture and has an FER/MFI mass ratio of at least 0.5:1, a concentration of the additive in relation to the base catalyst inventory is greater than or equal to 2% w/w, a concentration of the MFI zeolite in relation to the base catalyst inventory is greater than or equal to 1% w/w, and a total concentration of the MFI zeolite and the FER zeolite in relation to the base catalyst inventory is from 2% to 4% w/w.

2. The process according to claim 1, wherein the hydrocarbon feedstock comprises one or more of a naphtha stream, a kerosene stream, a diesel stream, a gas oil stream, an effluent from distillation of petroleum, an effluent from a delayed coking unit, an effluent from a hydrocracking unit or an effluent from a hydrotreating unit.

3. The process according to claim 1, wherein the hydrocarbon feedstock comprises recycles of C4 and C5 streams of one or more refining units selected from the group consisting of fluid catalytic cracking units, delayed coking units, hydrocracking units and hydrotreating units.

4. The process according to claim 1, wherein the hydrocarbon feedstock exhibits initial boiling points above −11° C.

5. The process according to claim 1, wherein conditions for catalytically cracking the hydrocarbon feedstock include a catalyst/oil ratio between 10 and 50 and a temperature between 550° C. and 750° C.

6. The process according to claim 1, wherein the MFI zeolite is a ZSM-5 zeolite.

* * * * *